United States Patent
Steinmetz

(10) Patent No.: US 9,198,690 B2
(45) Date of Patent: Dec. 1, 2015

(54) TEMPORARY FILTER RETRIEVAL APPARATUS AND METHOD

(71) Applicant: BiO2 Medical, Inc., San Antonio, TX (US)

(72) Inventor: Jeffrey N. Steinmetz, Arvada, CO (US)

(73) Assignee: BIO2 MEDICAL, INC., Golden, CO (US)

( * ) Notice: Subject to any disclaimer, the term of this patent is extended or adjusted under 35 U.S.C. 154(b) by 184 days.

(21) Appl. No.: 13/918,870

(22) Filed: Jun. 14, 2013

(65) Prior Publication Data

US 2014/0236215 A1    Aug. 21, 2014

Related U.S. Application Data

(63) Continuation of application No. 13/769,138, filed on Feb. 15, 2013.

(51) Int. Cl.
*A61M 29/00* (2006.01)
*A61B 17/50* (2006.01)
*A61F 2/01* (2006.01)

(52) U.S. Cl.
CPC . *A61B 17/50* (2013.01); *A61F 2/01* (2013.01); *A61F 2002/011* (2013.01)

(58) Field of Classification Search
CPC .............. A61M 25/0668; A61M 2025/0188; A61F 2/013; A61F 2002/011; A61F 2/01; A61B 17/50
See application file for complete search history.

(56) References Cited

U.S. PATENT DOCUMENTS

| 5,695,470 A * | 12/1997 | Roussigne et al. | 604/116 |
| 7,041,117 B2 | 5/2006 | Suon et al. | 606/200 |
| 2002/0022858 A1 * | 2/2002 | Demond et al. | 606/200 |
| 2003/0078519 A1 | 4/2003 | Salahieh et al. | 600/585 |
| 2004/0254602 A1 * | 12/2004 | Lehe et al. | 606/200 |
| 2006/0293696 A1 * | 12/2006 | Fahey et al. | 606/127 |
| 2009/0062840 A1 | 3/2009 | Angel | 606/200 |
| 2009/0088790 A1 | 4/2009 | Parodi et al. | 606/200 |
| 2009/0099574 A1 | 4/2009 | Fleming, III | 606/213 |
| 2010/0217304 A1 | 8/2010 | Angel et al. | 606/200 |
| 2011/0295306 A1 | 12/2011 | Blatter | 606/200 |

OTHER PUBLICATIONS

International Search Report issued in corresponding foreign application, pp. 1-6 (Jun. 18, 2014).

Decousus, Herve, et al., "A clinical trial of vena caval filters in the prevention of pulmonary embolism in patients with proximal deep-vein thrombisis" *The New England Journal of Medicine* 338(7): 409-415 (Feb. 12, 1998).

Lin, Peter H., et al., "Vena caval filters in the treatment of acute DVT" *Endovascular Today* pp. 40-50 (Jan. 2005).

* cited by examiner

*Primary Examiner* — Gregory Anderson
(74) *Attorney, Agent, or Firm* — David G. Rosenbaum; J. Peter Paredes; Rosenbaum IP, P.C.

(57) ABSTRACT

A temporary vena cava filter retrieval apparatus includes an introducer sheath for establishing access into a vessel via a patient access site and a retrieval sheath having a diameter sufficiently small to pass through the introducer sheath and sufficiently large to accommodate a partially or fully uncollapsed filter.

11 Claims, 4 Drawing Sheets

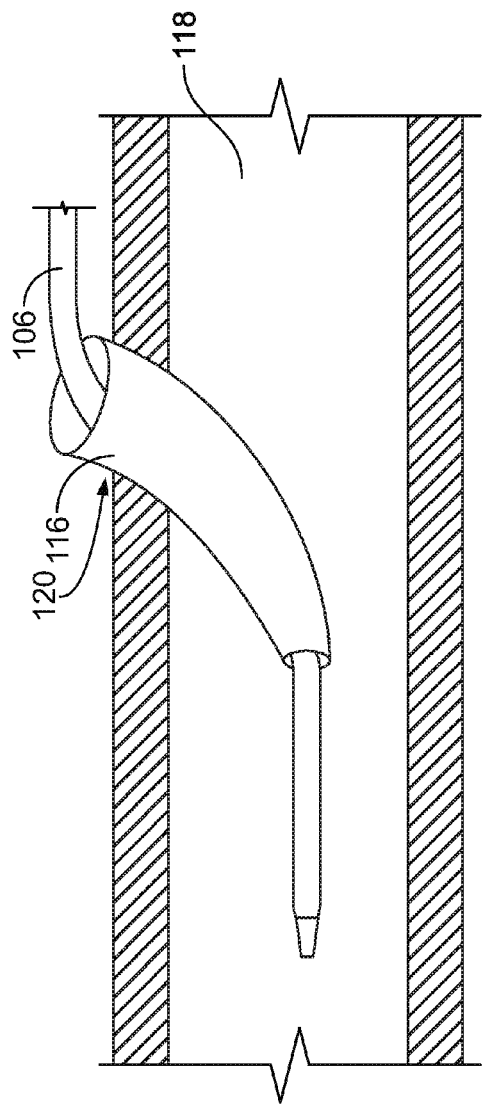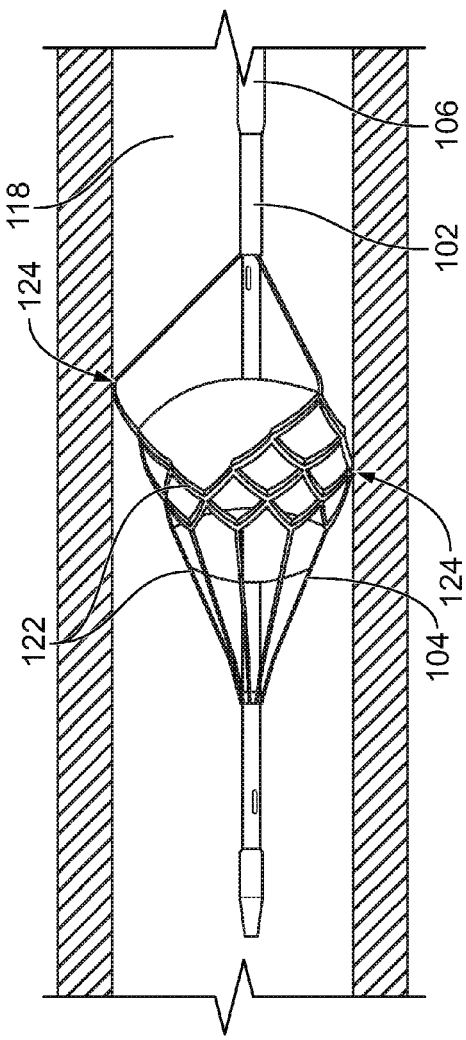
FIG. 2
FIG. 3

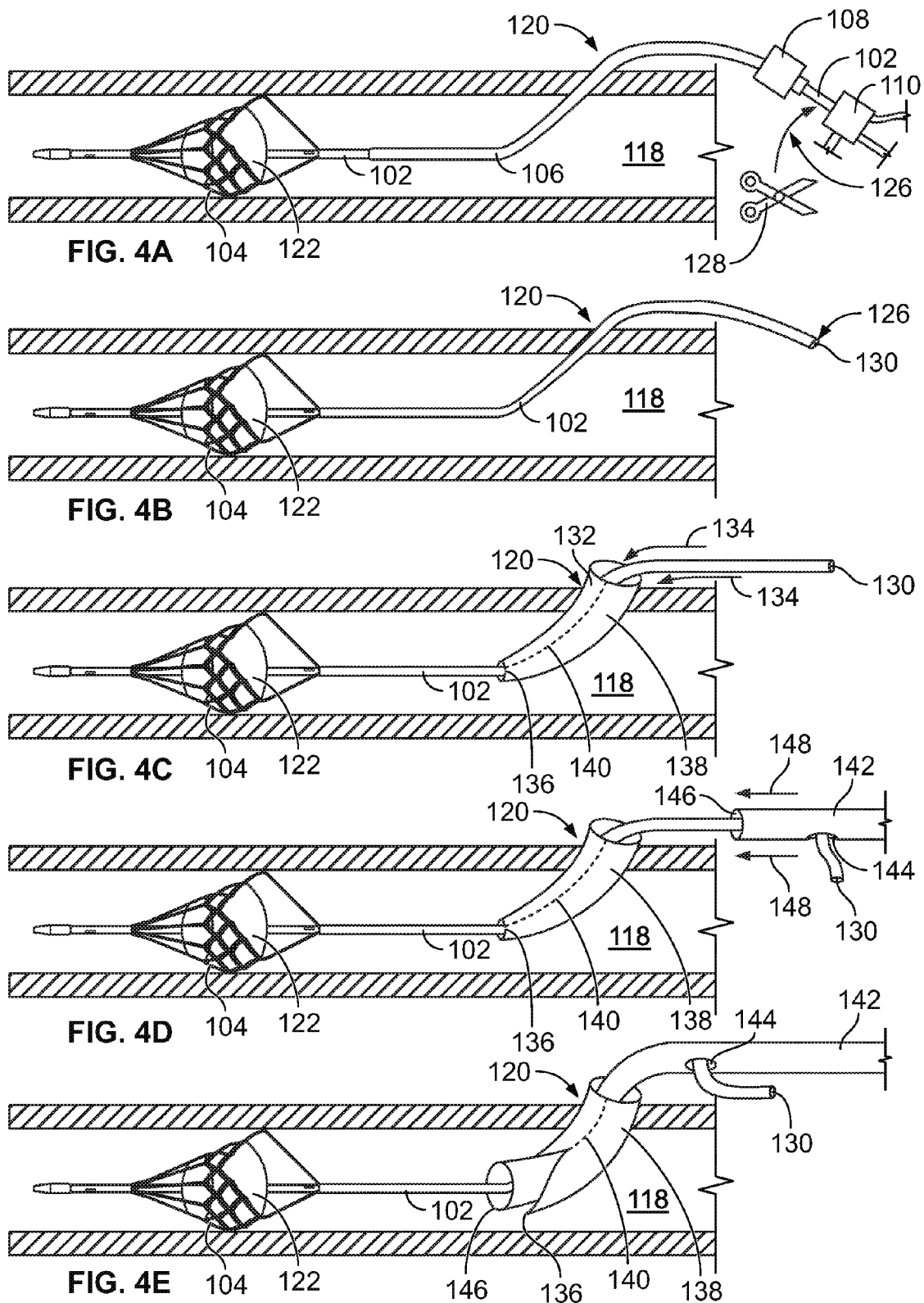

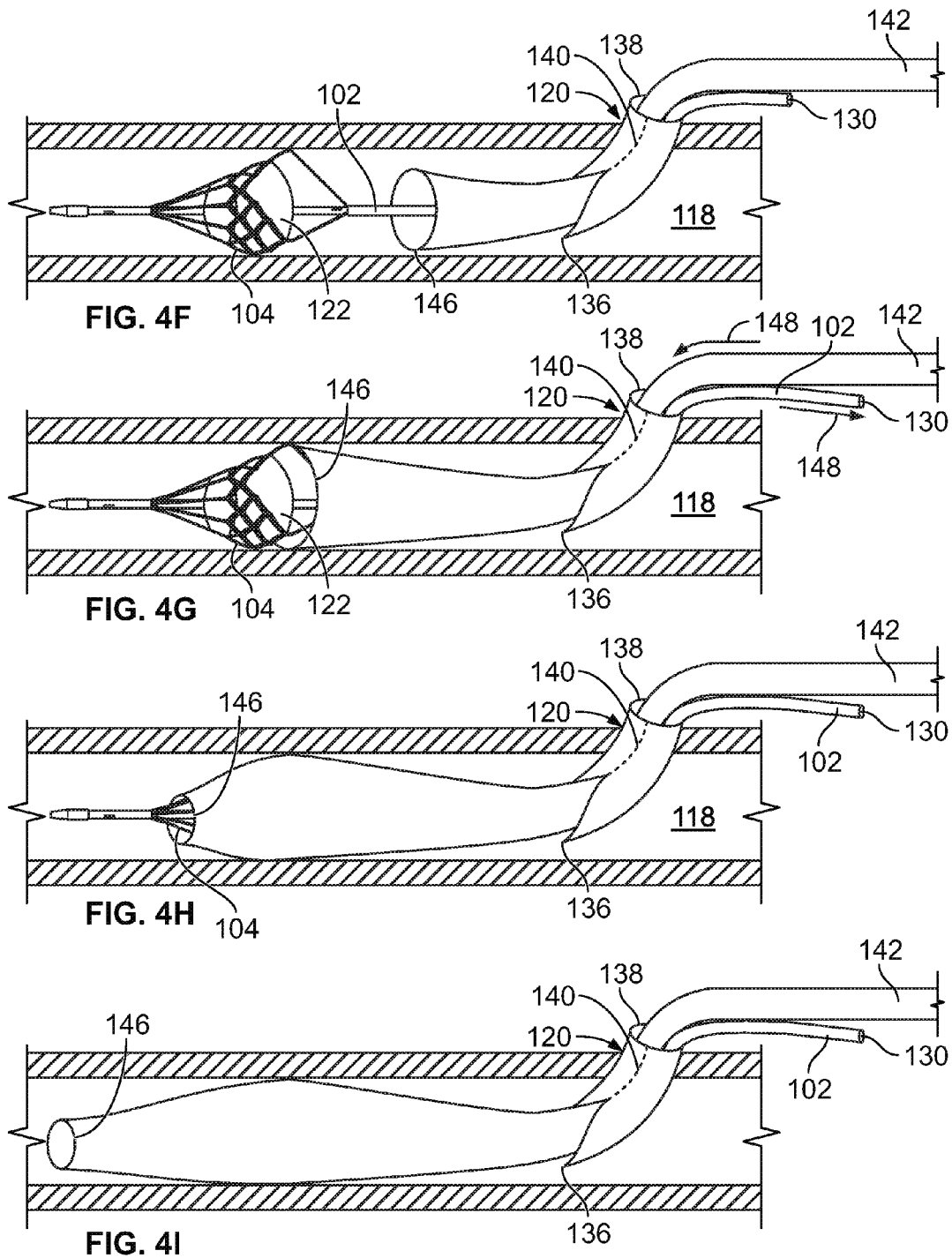

TEMPORARY FILTER RETRIEVAL APPARATUS AND METHOD

CROSS-REFERENCE TO RELATED APPLICATIONS

This application is a continuation application from U.S. patent application Ser. No. 13/769,138, filed Feb. 15, 2013, which is incorporated by reference in its entirety.

BACKGROUND OF THE INVENTION

The present invention pertains generally to the field of vascular filters for capturing embolic material in the blood flow. More particularly, the present invention relates to withdrawal of a temporary vena cava filter ("VCF") disposed near the distal end of a catheter having a catheter body and an outer sheath concentrically disposed over the catheter body.

The accepted standard of care for patients with venous thromboembolism (VTE) is anticoagulant therapy. Inferior vena cava (IVC) filters are reserved for those patients who fail anticoagulant therapy, or have a complication or contraindication to anticoagulant therapy. Until the early 1970's, the only method of IVC interruption was surgical, either by clipping, ligation, or plication. The first clinical experience of an endoluminally-placed device to interrupt IVC flow was reported by Mobin-Uddin et al. in 1969. However, it was not until the introduction of a stainless steel umbrella-type filter by Greenfield et al. in 1973 that an effective method of endoluminally trapping emboli while simultaneously preserving IVC flow became possible. Indeed, for many years, the Greenfield filter set a benchmark by which newer filters were measured. Early generations of filters were inserted by surgical cut-down and venotomy. Eventually filters were able to be inserted percutaneously: initially through large 24 Fr sheaths, though newer generations of filters are able to be delivered through 6 Fr systems.

Despite the safety and efficacy of modern day filters, systemic anticoagulation remains the primary treatment for VTE. Either unfractionated or low molecular weight heparin followed by three months of oral anticoagulation in patients with proximal deep venous thrombosis (DVT) is approximately 94% effective in preventing pulmonary embolism (PE) or recurrent DVT. The routine placement of IVC filters in addition to anticoagulation in patients with documented DVT was investigated by Decousus et al. in a randomized trial. Decousus H, Leizorovicz A, Parent F, et al. A clinical trial of vena caval filters in the prevention of pulmonary embolism in patients with proximal deep-vein thrombosis. *N Engl J Med* 1998; 338:409-415. This study revealed that the use of a permanent filter in addition to heparin therapy significantly decreased the occurrence of PE within the first 102 days compared to those without a filter. However, no effect was observed on either immediate or long-term mortality, and by 2 years, the initial benefit seen in the group of patients with filters was offset by a significant increase in the rate of recurrent DVT.

Despite the efficacy of anticoagulant therapy in the management of VTE, there are certain situations and conditions in which the benefits of anticoagulation are outweighed by the risks of instituting such a therapy. These include contraindications and complications of anticoagulant therapy. In such circumstances, there may be absolute or relative indications for filter insertion.

Currently, there are eight different types of permanent cava filters that are FDA approved. These include the Bird's Nest filter (Cook Incorporated, Bloomington, Ind.), Vena Tech LGM filter (B. Braun, Bethlehem Pa.), Vena Tech LP (B. Braun), Simon Nitinol filter (Bard, Covington, Ga.), Titanium Greenfield filter (Boston Scientific, Natick Mass.), Over-the-Wire Greenfield filter (Boston Scientific), TrapEase filter (Cordis Corp.) and the Gunther Tulip filter (Cook Inc.).

Well-founded concerns over the long-term complications of permanent IVC filters, particularly in younger patients in need of PE prophylaxis with a temporary contraindication to anticoagulation, has led to the development of temporary and retrievable filters. Temporary filters remain attached to an accessible transcutaneous catheter or wire. These have been used primarily in Europe for PE prophylaxis during thrombolytic therapy for DVT. Currently these devices are not approved for use in the United States. Retrievable filters are very similar in appearance to permanent filters, but with modifications to the caval attachment sites and/or hooks at one end that can facilitate their removal. Retrievable filters are currently available in the United States, examples of these as set forth in Endovascular Today's 2012 Buyer's Guide include the ALN Optional Filter (ALN), Option (Argon Medical Devices) Gunther Tulip (Cook Inc.), Celect and Opt Ease (Cordis Corp.), and Eclipse and Meridian nitinol filters (Bard Peripheral Vascular, Tempe, Ariz.). 2012 Buyer's Guide, *Endovascular Today* 2011; December: 98. The time limit of retrievability is in part dependant on the rate of endothelialization of the device, which typically occurs within 2 weeks. However, differences in design may extend the time period in which the filter may be safely retrieved.

Currently no consensus exists as to which patients have an indication for a retrievable filter. However, it is generally accepted that patients at high risk for pulmonary embolism or with documented PE and with a temporary contraindication to anticoagulation are candidates.

Certain circumstances preclude the placement of a filter in the infrarenal IVC. This includes thrombus extending into the infrarenal IVC, renal vein thrombosis or pregnancy. The safety of suprarenal placement of IVC filters is well documented, with no reported instances of renal dysfunction and no differences in the rates of filter migration, recurrent PE or caval thrombosis.

The rate of upper extremity DVT is on the rise. This is predominantly due to an increasing number of patients having short- and long-term upper extremity catheters. In one study, 88% of patients found to have an upper extremity DVT had a central venous catheter present at the site of thrombosis at the time of diagnosis or within the previous two weeks. Pulmonary embolism may complicate upper extremity DVT in 10-16% of cases. In patients who have such a complication or contraindication to anticoagulation, a filter can be safely placed immediately below the confluence of the brachiocephalic veins. However, misplacement of an SVC filter is theoretically more likely than with an IVC filter because of the relatively short target area for deployment.

The most common imaging modality used for filter insertion is fluoroscopy, performed either in an interventional suite or an operating room. Bedside placement of filters has inherent advantages, particularly for critically ill patients in intensive care settings where transport can be avoided. Portable fluoroscopy, surface duplex ultrasound and intravascular ultrasound (IVUS) have all been used to assist with bedside filter placement.

VCF placement frequently occurs concomitantly with central access line placement or in critically ill patients that already have a central access line in place. Heretofore, however, there have been few devices which combine the function of a central access catheter and a removable VCF. Examples of a catheter coupled to a VCF that is useful both as a central venous access catheter for administration of intravenous fluids, bioactive agents, contrast agents, flushing agents, pressurized fluids for mechanical thrombolysis and/or withdrawal of blood samples and for capture of thrombus or emboli are presented in U.S. patent application Ser. No. 11/849,225, filed Aug. 31, 2007, and U.S. patent application Ser. No. 12/684,839, filed Jan. 8, 2010, both of which are hereby incorporated in their entirety herein. Thus, the catheter in accordance with the present invention may be a central access catheter or may simply be a catheter without central access functionality.

SUMMARY OF THE INVENTION

In one aspect of the present invention there is provided a temporary venous filter retrieval apparatus, comprising a first sheath for establishing access to a patient's blood vessel and a second sheath deliverable through a lumen of the first sheath and of sufficient diameter to capture a wholly or partially uncollapsed venous filter residing with a patient's vasculature.

In accordance with another aspect of the present invention there is provided a method for retrieving a vena cava filter in use at a treatment site which consists of delivering a retrieval sheath concentrically over a catheter attached to the vena cava filter, the retrieval sheath being capable of enveloping a wholly or partially uncollapsed vena cava filter there within for removal from the patient.

The present invention may be configured for either a femoral approach or a jugular approach to the inferior vena cava. VCFs are typically deployed infrarenaly, but may also be deployed suprarenaly. It will be understood that within the inferior vena cava blood flow is superior, i.e., toward the patients head. Thus, in all embodiments, the VCF will be positioned so that it opens inferiorly, i.e., away from the patient's head and toward the direction of the blood flow. It will be appreciated, therefore, that in the present invention, the VCF will have a different axial orientation on the central access catheter depending upon whether the device is intended for use in a femoral approach or a jugular approach.

Regardless of the axial orientation of the VCF, embolic material captured within the VCF may be of sufficient size so as to inhibit the filter from being fully collapsed for withdrawal through the outer sheath. Thus, there exists the potential need for retrieval of the VCF via an alternative to the outer sheath.

BRIEF DESCRIPTION OF THE DRAWINGS

FIG. 2 is an illustration of the use of an introducer sheath at a treatment site.

FIG. 3 is an illustration of embolus captured within a VCF.

FIG. 4A is an illustration of a step in an alternative method of VCF retrieval.

FIG. 4B is an illustration of another step in an alternative method of VCF retrieval.

FIG. 4C is an illustration of a further step in an alternative method of VCF retrieval.

FIG. 4D is an illustration of yet another step in an alternative method of VCF retrieval.

FIG. 4E is an illustration of a still further step in an alternative method of VCF retrieval.

FIG. 4F is an illustration of another step in an alternative method of VCF retrieval.

FIG. 4G is an illustration of yet another step in an alternative method of VCF retrieval.

FIG. 4H is an illustration of a further step in an alternative method of VCF retrieval.

FIG. 4I is an illustration of yet a further step in an alternative method of VCF retrieval.

DETAILED DESCRIPTION OF THE PREFERRED EMBODIMENTS

Figure 1A:
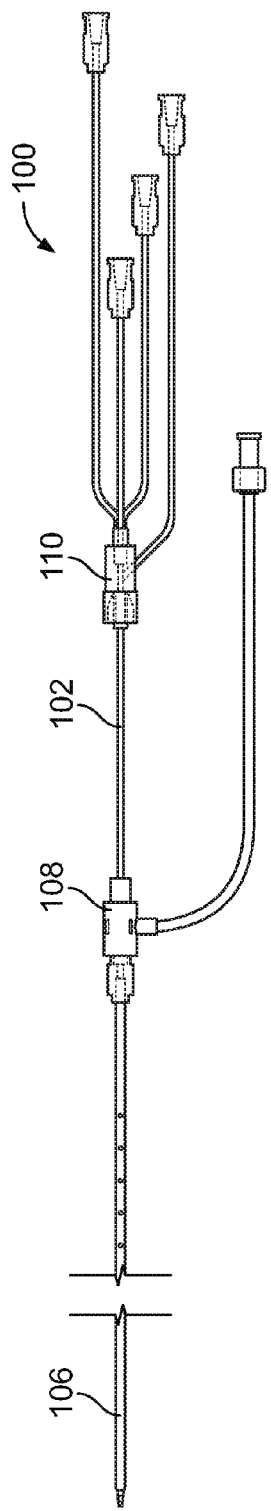
FIG. 1A is a side elevational view of an exemplary catheter with a VCF in an unexpanded state.
Figure 1B:
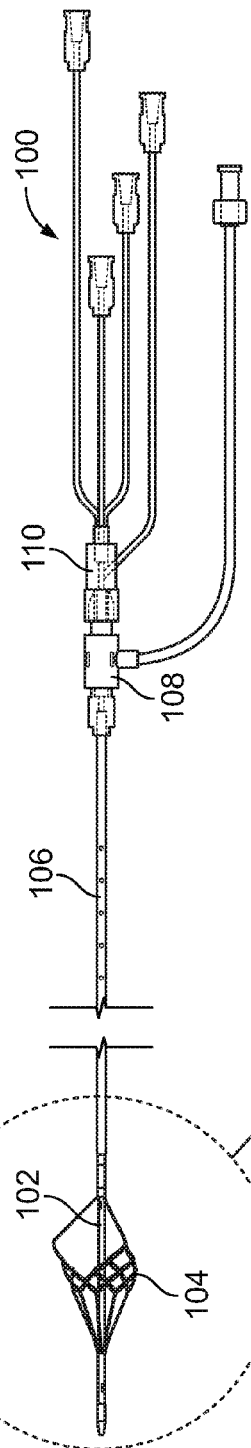
FIG. 1B is a side elevational view of the exemplary catheter of FIG. 1A with the VCF in an expanded state.
Figure 1C:
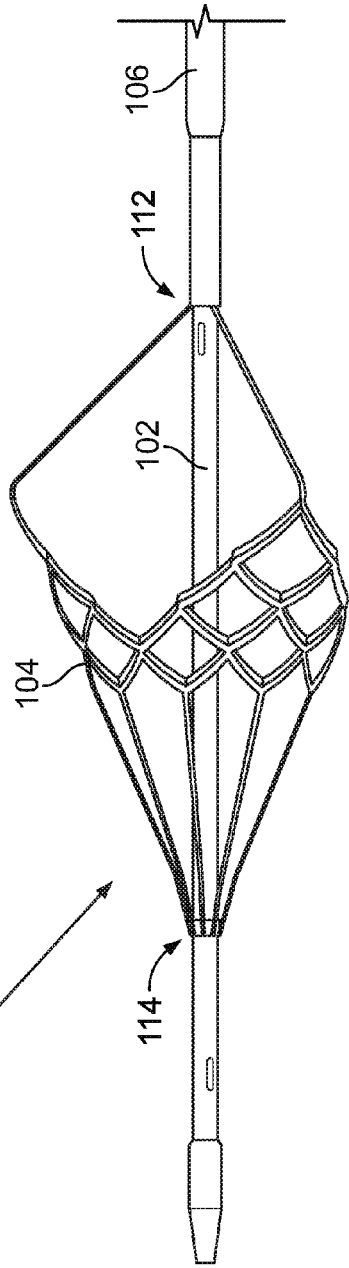
FIG. 1C is an expanded view of the distal end of the catheter of FIG. 1B.

Referring to FIGS. 1A-1C, an exemplary catheter 100 is composed generally of a catheter body 102 and a VCF 104 disposed generally concentric relative to the catheter body 102. An outer sheath 106 is concentrically disposed over the catheter body 102 such that relative axial movement of the catheter body 102 and the outer sheath 106 either captures the VCF 104 within the outer sheath 106 or exposes the VCF 104, as illustrated in FIGS. 1A and 1B, respectively.

As used in this application, unless otherwise specifically stated, the terms "proximal" and "distal" are intended to refer to positions relative to the longitudinal axis of the catheter body 102. Those skilled in the art will understand that the catheter body 102 has a distal end which is first inserted into the patient and a proximal end which is opposite the distal end. Additionally, the terms "inferior" or "inferiorly" are intended to refer to the anatomic orientation of being in a direction away from the patient's head while the terms "superior" or "superiorly" are intended to refer to the anatomic orientation of being toward the patient's head. Additionally, the term "catheter" is intended to refer to central venous access catheters, non-central venous access catheters as well as non-tubular members capable of carrying a VCF.

The outer sheath 106 terminates in an annular opening at a distal end thereof between an inner surface of the outer sheath 106 and an outer surface of the catheter body 102 and at distal hub 108. The catheter body 102 extends through a central bore in the distal hub 108 and passes through a central lumen of the outer sheath 106. A proximal hub 110 is coupled to a proximal end of the catheter body 102. The proximal hub 110 and the distal hub 108 are removably engageable with each other as described in U.S. Provisional Patent Application Ser. No. 61/322,242, filed Apr. 8, 2010, and hereby incorporated in its entirety herein.

Depending upon the approach orientation of the VCF 104, i.e., jugular or femoral, a proximal end 112 or distal end 114 of the VCF 104 may either be fixed or moveable relative to the catheter body 102. Alternatively, the VCF 104 may have only a proximal end 112 which is fixed to the catheter body 102.

In one embodiment, apices at the proximal or distal ends 112, 114 of the VCF 104 are joined by a generally cylindrical collar that serves to moveably couple the VCF 104 to the catheter body 102. The generally cylindrical collar is concentrically engaged about the catheter body 102 and may be axially movable thereupon, or is formed by connections between adjacent pairs of longitudinal strut-like structural members which circumscribe a circumference of the catheter body 102. Alternatively, the apices at the proximal or distal ends 112, 114 of the VCF 104 may be independent or unjoined. In this later circumstance, no generally cylindrical collar will be employed and the apices will be arrayed about the circumference of the catheter body member 102 and moveable thereupon.

While the present invention is not limited to specific dimensional sizes of either the catheter body member 102 or the outer sheath 106, an exemplary outer diameter size of the outer sheath 106 is between 8 Fr (2.7 mm) and 9 Fr (3.0 mm), while an exemplary outer diameter size of the catheter body 102 is between 6 Fr (2.0 mm) and 7Fr, and the expanded diameter of the VCF 104 is between about 25 to 40 mm.

To facilitate percutaneous introduction of the catheter 100, a physician may optionally elect to employ an introducer sheath 116 as a vascular access conduit for the catheter 100, as illustrated in FIG. 2. The introducer sheath 116 is inserted into a vessel 118, for example, a vein or artery 118, via a patient access site 120. Once the introducer sheath 116 is placed, the catheter 100 may be introduced through a central lumen of the introducer sheath 116 and into the patient's vasculature. The presence of the VCF 104 at the distal end of the catheter body 102 creates a region of relatively lower flexibility and the practitioner may determine it beneficial to employ the introducer sheath 116 for vascular access.

When used, the introducer sheath 116 is first placed into the vessel 118 via the patient access site 120 in a normal manner for introducing a central venous line, such as by the Seldinger technique. Specifically, after accessing the vessel 118 using a large bore needle, under local anesthesia, a guidewire is inserted through the needle bore and passed into the vessel 118. Once the guidewire is positioned, the needle is withdrawn, and a dilator (not shown) together with the introducer sheath 116 is introduced over the guidewire. Once the introducer sheath 116 is positioned at a desired location within the vessel 118 under radiography, the dilator may be removed from the patient. Radiopaque markers associated with the introducer sheath 116 may be employed to assist in positional visualization of the distal end of the introducer sheath 116.

The outer sheath 106 constrains the VCF 104 in a collapsed state (see FIG. 1A) during its passage through the introducer sheath to a treatment site within the patient's vasculature. Once the distal end of the catheter body 102 reaches the treatment site, the VCF 104 is deployed to an expanded state (see FIGS. 1B and 1C) by proximally retracting the outer sheath 106 relative to the catheter body 102. The deployed VCF 104 captures emboli that may have been released during treatment at the treatment site.

Ordinary retrieval and removal of the VCF 104 is accomplished by withdrawing the catheter body 102 carrying the VCF 104 into the outer sheath 106 to collapse the VCF 104. Once collapsed within the outer sheath 106, the VCF 104, the catheter body 102, and the outer sheath are collectively withdrawn from the patient. However, situations may arise where the ordinary retrieval procedure does not work.

For example, referring to FIG. 3, the VCF 104 may be inhibited from being fully collapsed and withdrawn into the outer sheath 106 by captured emboli 122 of sufficient size or hardness. Such an uncollapsed VCF 104 makes removal of the VCF 104 problematic for several reasons. First, an uncollapsed VCF 104 remains exposed to the lumen of the vessel 118 and to the blood flow therethrough. Thus, an uncollapsed VCF 104 may detrimentally contact the lumenal surfaces causing unnecessary damage thereto. Further, an uncollapsed VCF 104 that is exposed to blood flow may release captured emboli 122 back into the blood flow, thereby defeating the purpose of the VCF 104. In more extreme cases, an uncollapsed VCF 104 may be stuck in place at the treatment site by being lodged against the luminal surface, for example, at points 124 in FIG. 3, of the vessel 118 such that any attempt at removal would cause damage to the lumenal surface. In other cases, it is contemplated that the VCF 104 may become so lodged in place at the treatment site as to make retrieval impossible without an alternative apparatus and method for retrieval.

Such an alternative method for VCF retrieval is illustrated in FIGS. 4A-4I. Starting with FIG. 4A, an especially large or hard embolus or emboli 122 is captured by the VCF 104 in the vessel 118. The distal and proximal hubs 108, 110 have been separated and the outer sheath 106 is being advanced distally over the catheter body 102 toward the VCF 104, which may be partially collapsed but is inhibited from further collapse by the presence of the emboli 122. At this point, the medical professional realizes there is a problem with collapse of the VCF 104 and orders that the alternative method described hereinbelow for retrieval is utilized. Accordingly, as a first step in the alternative method for retrieval of the VCF 104, the catheter body 102 is severed at a point 126 between the distal and proximal hubs 108, 110 by a cutting implement 128, for example a scalpel or scissors 128, as illustrated in FIG. 4A, while maintaining hemostasis, such as by clamping, then occluding the terminal opening of the catheter body 102.

Referring to FIG. 4B, subsequent to the severing of the catheter body 102, the outer sheath 106 and the proximal hub 110 are pulled off the catheter body 102, leaving the point 126 where the catheter body 102 was severed at the proximal end 130 of the catheter body 102. At this point in the method, there is no obstruction along the abluminal surface of the catheter body between the proximal end 130 and the patient access site 120.

Referring to FIG. 4C, an introducer sheath 132, as known in the art, is slid over the proximal end 130 of the catheter body 102 and advanced toward the patient access site 120 in the direction indicated by arrows 134. The introducer sheath 132 includes a first end 136 disposed toward the patient access site 120 and an opposing second end 138 disposed away from the patient access site 120. The introducer sheath 132 is designed to break apart at a frangible section 140 which may be a weakened section or score line that permits the introducer sheath 132 to open along the frangible section 140. When another tube having an outer diameter greater than the inner diameter of the introducer sheath is introduced within the introducer sheath, 132, the frangible section 140 will open permitting passage of the other tube through the introducer sheath 132. Introducer sheath 132 may have a tapered generally conical shape along its longitudinal axis to facilitate introduction into the patient's vasculature as well as increased pressure to separate the frangible section 140 as the other tube traverses within the introducer sheath 132. The frangible section 140 may be oriented in any direction as desired with regard to a longitudinal axis of the peel-away introducer sheath 132, for example, generally aligned with the longitudinal axis, as illustrated in FIGS. 4B-4I.

Referring to FIG. 4D, the first end 136 of the introducer sheath 132 is designed to penetrate the access site 120 around the catheter body 102. The introducer sheath 132 provides access to the vessel 118 by providing a smooth pathway between the catheter body 102 and the patient access site 120 for a second sheath 142 to slide over the catheter body 102. The second sheath 142, which functions to capture and retrieve the VCF 104, has an inner diameter which is sufficient to accommodate the wholly or partially uncollapsed VCF 104 therein. Given that the second sheath 142 is long enough to reach to the VCF 104, it is preferable that the second sheath 142 include a side lumen 144 that is sufficiently large to pass the catheter body 102 therethrough. The second sheath 142 including the side lumen 144 may sometimes be referred to in the art as a rapid-exchange sheath 142. The proximal end 130 of the catheter body 102 is directed through a distal end 146 of the rapid-exchange sheath 142 and out the side lumen 144. The rapid-exchange sheath 142 may thus be directed along the catheter body 102 in the direction of the patient access site 120 as indicated by arrows 148. It will be understood by those skilled in the art, that the catheter body 102 thus serves a guidance or tracking function for the second sheath as it is being delivered over the catheter body 102 to capture and retrieve the VCF 104.

Still referring to FIG. 4D, to ensure that the break point of the introducer sheath 132 is not outside the patient access site 120, the introducer sheath 132 is pushed into the patient access site 120 to a depth sufficient such that the diameter of the introducer sheath 132 at the surface of the patient access site 120 is sufficiently large to accommodate the second sheath 142. At this depth of penetration of the introducer sheath 132, the second sheath 142 can penetrate the patient access site 120 before the introducer sheath 132 is forced to break at the break point. The introducer sheath 132 thus functions to facilitate introduction of the second sheath 142 sheath into the vessel 118.

Referring to FIG. 4E, the second sheath 142 has been introduced into the vessel 118 over the catheter body 102 and through the peel-away introducer sheath 132. The first end 136 of the introducer sheath 132 has been split apart along the frangible section 140. The now split apart introducer sheath 132 may be removed at this point in the method; however, because the peel-away introducer sheath 132 continues to facilitate passage of the second sheath 142 through the patient access point 120 by providing less frictional resistance to the second sheath 142 than does the patient access site 120, it may be preferable to leave the introducer sheath 132 in place.

Referring to FIG. 4F, the second sheath 142 has been advanced within the vessel 118 such that the distal end 146 is proximate the VCF 104. In this embodiment, the introducer sheath 132 has been left in place at the patient access site 120. With the second sheath 142 proximate the VCF 104, the next step is to capture the VCF 104 within the second sheath 142.

Referring to FIG. 4G, the second sheath 142 is pushed distally and/or the catheter body 102 is pulled proximally as indicated by arrows 148 to slide the second sheath 142 over the uncollapsed VCF 104. FIG. 4G illustrates the VCF 104 partially within the distal end 146 of the second sheath 142. Once the VCF 104 is at least partially within the distal end 146, the second catheter 142 and the catheter body 102 may be extracted from the vessel 118 together, thus safely removing the uncollapsed VCF 104 and the captured emboli 122 from the patient via the patient access site 120. Continuing to advance the second sheath 142 and the catheter body 102 relative to each other, as indicated by the arrows 148, slides the uncollapsed VCF 104 further into the second sheath 142, as illustrated in FIG. 4H. Ultimately, the uncollapsed VCF 104 may be pulled entirely within the second sheath 142, as illustrated in FIG. 4I. After withdrawal of the VCF 104 such that the VCF 104 is safely contained within the second sheath 142, if the peel-away introducer sheath 132 has not already been removed, the peel-away introducer sheath 132 may now be removed from the patient access site to complete the alternative method.

The second sheath 142 may be made of a wide variety of biocompatible materials that exhibit sufficient column strength for adequate pushability and pullability without undue compression or elongation during delivery or retrieval of the second sheath 142. Additionally the second sheath 142 may be made of biocompatible material(s) that permit the second sheath to have a relatively smaller diameter, but exhibit diametric expandability at a distal end thereof to permit the second sheath 142 to conform to and envelope an enlarged VCF 104. Thus the second sheath 142 may exhibit some degree of moderate elasticity or moderate plasticity sufficient to achieve the above purposes. Suitable materials contemplated for the present invention include solid wall or braided polymeric materials, such as polyimide, PBAX, polytetrafluoroethylene, polyethylene, silicone, or other similar biocompatible polymeric materials, or biocompatible metals such as stainless steel, NITINOL, cobalt-chromium-molybdenum shape memory materials which are either braided or formed into a series of convoluted members forming walls of an elongate tubular structure.

There has been described an alternative method for the removal of a filter that may be inhibited from being fully collapsed in accordance with the foregoing disclosure which includes, generally, a catheter body 102, a VCF 104, a peel-away introducer sheath 132, a second sheath 142, and an implement 128, for example, scissors, for cutting the catheter body 102. The peel-away introducer sheath 132 may be removed at any point in the method following the introduction of the second sheath 142 into the vessel 118, or the peel-away introducer sheath 132 may be left in place at the patient access site 120. The catheter body 102 and the second sheath 142 with the VCF 104 at least partially within the distal end thereof may be removed together at any point in the method following the VCF 104 being at least partially pulled into the second sheath 142. These and other aspects of the present invention are provided by way of non-limiting examples, with the claims appended hereto serving to define the scope of the subject matter regarded as the invention.

What is claimed is:

1. A method for retrieving an at least partially uncollapsed filter disposed on a catheter body when the venous filter and a portion of the catheter body are within a blood vessel, comprising:

threading an introducer sheath over a proximal end of the catheter body external the patient's body;

inserting a first end of the introducer sheath into a vascular access site and into the patient's vasculature;

severing a portion of the proximal end of the catheter body while maintaining hemostasis;

threading a non-split rapid exchange retrieval sheath over the proximal end of the catheter body, wherein the non-split rapid exchange retrieval sheath further comprises a side lumen through which the proximal end of the catheter body passes and exits the non-split rapid exchange retrieval sheath proximal to a distal end of the retrieval sheath;

advancing the non-split rapid exchange retrieval sheath through the introducer sheath and toward a distal end of the catheter body proximate the venous filter and within a blood vessel, the non-split rapid exchange retrieval sheath having a diametrically expansible section at the distal end being radially expandable from a smaller diameter to a larger diameter;

enveloping the at least partially uncollapsed filter within the larger diameter of the diametrically expansible section at the distal end of the retrieval sheath thereby capturing the uncollapsed venous filter within the retrieval sheath; and concurrently withdrawing the non-split rapid exchange retrieval sheath, the venous filter and the catheter body from the patient.

2. The method of claim 1, further including the step of removing the introducer sheath.

3. The method of claim 1, further including the step of passing a proximal portion of the catheter body through the side lumen of the non-split rapid exchange retrieval sheath.

4. The method of claim 3, wherein step (d) further includes the step of advancing the non-split rapid exchange retrieval sheath along the catheter body toward the venous filter.

5. The method of claim 1, wherein the introducer sheath has a generally conical shape.

6. The method of claim 5, further comprising disposing the introducer sheath at a depth such that the diameter of the introducer sheath at an access site is sufficiently large to accommodate the retrieval sheath therein.

7. The method of claim 1, further comprising breaking apart a frangible section of the introducer sheath during insertion of the retrieval sheath therethrough.

8. The method of claim 5, wherein the frangible section of the introducer sheath resides within the patient's vasculature during use thereof.

9. The method of claim 1, further comprising expanding the non-split rapid exchange retrieval sheath over the uncollapsed venous filter.

10. The method of claim 1, wherein the uncollapsed venous filter is inhibited from being fully collapsed.

11. The method of claim 1, wherein the uncollapsed venous filter is partially collapsed.

\* \* \* \* \*